(12) United States Patent
Lee et al.

(10) Patent No.: US 10,058,583 B2
(45) Date of Patent: Aug. 28, 2018

(54) HERBAL COMPOSITIONS FOR TREATING NEUROLOGICAL DISEASES AND IMPROVING MEMORY IMPAIRMENT

(75) Inventors: Doo Suk Lee, Anyang-si (KR); Dong Sik Kim, Hwaseong-si (KR); Seon Hee Kim, Gwacheon-si (KR)

(73) Assignee: VIROMED CO., LTD., Seoul (KR)

( * ) Notice: Subject to any disclaimer, the term of this patent is extended or adjusted under 35 U.S.C. 154(b) by 0 days.

(21) Appl. No.: 14/007,095

(22) PCT Filed: Mar. 29, 2012

(86) PCT No.: PCT/KR2012/002330
§ 371 (c)(1),
(2), (4) Date: Sep. 24, 2013

(87) PCT Pub. No.: WO2012/134194
PCT Pub. Date: Oct. 4, 2012

(65) Prior Publication Data
US 2014/0023677 A1    Jan. 23, 2014

(30) Foreign Application Priority Data

Mar. 29, 2011 (KR) ........................ 10-2011-0028086

(51) Int. Cl.
| *A61K 36/9066* | (2006.01) |
| *A61K 36/77* | (2006.01) |
| *A61K 36/8988* | (2006.01) |
| *A61K 36/537* | (2006.01) |
| *A61K 36/88* | (2006.01) |
| *A61K 45/06* | (2006.01) |

(52) U.S. Cl.
CPC ........ *A61K 36/9066* (2013.01); *A61K 36/537* (2013.01); *A61K 36/77* (2013.01); *A61K 36/88* (2013.01); *A61K 36/8988* (2013.01); *A61K 45/06* (2013.01)

(58) Field of Classification Search
None
See application file for complete search history.

(56) References Cited

U.S. PATENT DOCUMENTS

| 2005/0142223 A1* | 6/2005 | Gong et al. ................... 424/728 |
| 2008/0260868 A1 | 10/2008 | Hendrix |
| 2009/0312413 A1 | 12/2009 | Song et al. |
| 2011/0318435 A1 | 12/2011 | Yang et al. |

FOREIGN PATENT DOCUMENTS

| CN | 1181966 A | 5/1998 |
| CN | 1462624 A | 12/2003 |
| CN | 1552838 A | 12/2004 |
| CN | 101543587 A | 9/2009 |
| CN | 101554238 A | 10/2009 |
| CN | 101601471 A | * 12/2009 |
| CN | 101829280 A | 9/2010 |
| CN | 101926459 A | 12/2010 |
| JP | 2009-511467 A | 3/2009 |
| JP | 2012-006906 A | 1/2012 |
| KR | 1020030071035 A | 9/2003 |
| KR | 20040015828 A | 2/2004 |
| KR | 100894415 B1 | 4/2009 |
| WO | WO-2007/043796 A1 | 4/2007 |

OTHER PUBLICATIONS

Cephalic 2014 http://www.ninds.nih.gov/disorders/cephalic_disorders/detail_cephalic_disorders.htm.*
Park et al., "The memory-enhancing effects of Euphoria longan fruit extract in mice," J Ethnopharmacol. 128(1):160-165 (2010).
International Search Report for PCT/KR2012/002330, dated Nov. 30, 2012 (4 pages).
Kim et al., "Neuroprotective effect of some plant extracts in cultured CT105-induced PC12 cells," Biol Pharm Bull. 29(10):2021-4 (2006).
Lee et al., "Ameliorating effects of HX106N, a water-soluble botanical formulation, on a(beta)25-35-induced memory impairment and oxidative stress in mice," Biol Pharm Bull. 37(6):954-60 (2014).
Yang et al., "Modified TLC bioautographic method for screening acetylcholinesterase inhibitors from plant extracts," J Sep Sci. 32(18):3257-9 (2009).
Wang Fei et al., "Effect of tanshinol extra on learning and memory fuction in mice," China Practical Medical. 3(24):132-33 (2008).
Zhou Benhong et al., "Effect of Gastrodia elata ectract on learning and memory of mice," Pharmacology and Clinics of Chinese Materia Medica. 3:32-3 (1994).
European Search Report for European Application No. 12762802.2, dated Dec. 1, 2014, Lee et al., "Herbal Compositions for Treating Neurological Diseases and Improving Memory Impairment," filed Mar. 29, 2012 (10 pages).
Japanese Office Action for Japanese Application No. 2014-502473, dated Nov. 11, 2014, Lee et al., "Herbal Compositions for Treating Neurological Diseases and Improving Memory Impairment," filed Mar. 29, 2012 (3 pages).
Rejection Decision for Chinese Application No. 201280016132.2, dated Jan. 6, 2017, Lee et al., "Herbal Compositions for Treating Neurological Diseases and Improving Memory Impairment," filed Mar. 29, 2012 (11 pages).

(Continued)

*Primary Examiner* — Terry Alan McKelvey
*Assistant Examiner* — Catheryne Chen
(74) *Attorney, Agent, or Firm* — Clark & Elbing LLP; Susan M. Michaud (57) ABSTRACT

The present invention relates to a composition for preventing or treating neurological diseases including an extract of *Euphoria longan* fruit, red sage and *Gastrodia elata* as an active ingredient. The composition of the present disclosure has a superior effect of inhibiting the activity of acetylcholinesterase (AChE), which hydrolyzes the neurotransmitter acetylcholine directly involved in impairment of cognitive function. In addition, the composition of the present disclosure is safe for the human body since the biologically safe extract of *Euphoria longan* fruit, red sage and *Gastrodia elata* is used as the active ingredient.

18 Claims, 6 Drawing Sheets

(56) References Cited

OTHER PUBLICATIONS

Senjo, "Usefulness of Gastrodia elata on Dementia," Journal of New Remedies & Clinics. 43(12):2645-51 (1994) (18 pages).
Wang Fei et al., "Effect of alcohol extract of red sage on learning and memory fuction in mice," China Practical Medical. 3(24):132-33 (2008). (English abstract provided).
Zhou Benhong et al., "Effect of Gastrodia elata extract on learning and memory of mice," Pharmacology and Clinics of Chinese Materia Medica. 3:32-3 (1994). (English abstract provided).

* cited by examiner

HERBAL COMPOSITIONS FOR TREATING NEUROLOGICAL DISEASES AND IMPROVING MEMORY IMPAIRMENT

CROSS-REFERENCE TO RELATED APPLICATIONS

This application is the U.S. national stage filing under 35 U.S.C. § 371 of International Application PCT/KR2012/002330, filed Mar. 29, 2012, which claims priority from Korean Patent Application 10-2011-0028086, filed Mar. 29, 2011.

BACKGROUND OF THE INVENTION

Field of the Invention

The present disclosure relates to a herbal composition for preventing or treating neurological diseases or improving brain or cognitive function. More particularly, it relates to a herbal composition for protecting nerve cells and improving neurological diseases, which includes an extract of *Euphoria longan* fruit, red sage and *Gastrodia elata*.

Background of Technique

Dementia refers to severe loss of global cognitive ability without disorder of consciousness, leading to loss of mental (intellectual) ability and ability for social activities. Dementia may be caused by various causes and is accompanied by memory impairment, speech impediment, disturbance in visuospatial ability, apraxia, agnosia, impairment of computational ability, frontotemporal lobar degeneration, disturbance in executive function, or the like.

Dementia can be classified into Alzheimer's dementia, vascular dementia and other dementia according to occurrence. Alzheimer's disease is the leading cause of dementia, accounting for about 50-60%. It is known that the impairment of cognitive function and damage of nerve cells in patients with dementia are related with disorder in transport, generation, secretion and removal of neurotransmitters. Representative neurotransmitters are acetylcholine and glutamate. It is reported that patients with dementia show decrease and reduced function of the neurotransmitter acetylcholine in brain tissues, which is important in learning and memory. Glutamate is an important excitatory neurotransmitter playing a key role in learning and memory in the central nervous system. It is known that excess glutamate accumulated around nerve cells can cause oxidative stress by inhibiting the synthesis of the antioxidant glutathione in the nerve cells or induce death of the nerve cells by causing influx of calcium ions via the N-methyl-D-aspartate (NMDA) receptor. Since the causes of dementia are various, medications for dementia target various routes. Typical example is the acetylcholinesterase (AChE) inhibitor which inhibits the reduction of the neurotransmitter acetylcholine directly involved in the impairment of cognitive function. Tacrine (Cognex®), donepezil (Aricept®), rivastigmine (Exelon®) and galantamine (Reminyl®) are examples. However, tacrine has the adverse effect of hepatotoxicity (Leonard, *World Psychiatry* 3: 84-88 (2004)), donepezil has adverse effects including nausea, vomiting and diarrhea (Burns et al., *Dement Geriatr Cogn Disord* 10: 237-244 (1999)), rivastigmine has central and peripheral cholinergic adverse effects at high concentrations (Leonard, *World Psychiatry* 3: 84-88, 2004), and galantamine has adverse effect in the gastrointestinal tract (Tariot et al., *Neurology* 54: 2269-2276, 2000). Other medications include memantine (Ebixa®) that acts on the glutamate receptor (Reisberg et al., *Am J Geriatr Psychiatry* 10:1-122 (2002)) as well as anti-inflammatory and antioxidant drugs. However, since the causes of dementia are diverse and not fully elucidated, treatments with the medications are only temporary or limited. In addition, although many patents about compositions for improving memory are published and issued in Korea, there is no sure cure yet. Accordingly, there is a strong need for the development of a medication of dementia having an excellent effect of preventing and treating the impairment of cognitive function with less adverse effects.

Throughout the specification, a number of publications and patent documents are referred to and cited. The disclosure of the cited publications and patent documents is incorporated herein by reference in its entirety to more clearly describe the state of the related art and the present disclosure.

SUMMARY OF THE INVENTION

The inventors of the present disclosure have explored natural materials capable of preventing or treating neurological diseases, especially dementia or memory impairment, that can be quickly absorbed into the human body without adverse effects. As a result, they have found out that a composition including an extract of *Euphoria longan* fruit, red sage and *Gastrodia elata* improves memory impairment and effectively protects nerve cells from substances causing neurological diseases, particularly dementia.

The present disclosure is directed to providing a pharmaceutical composition for preventing or treating neurological diseases.

The present disclosure is also directed to providing a food composition for improving neurological diseases.

The present disclosure is also directed to providing a method for preventing or treating neurological diseases.

The present disclosure is also directed to providing a food composition for improving brain or cognitive function.

The present disclosure is also directed to providing a method for improving brain or cognitive function.

Other features and aspects will be apparent from the following detailed description, drawings and claims.

DETAILED DESCRIPTION OF THE INVENTION

In one general aspect, the present disclosure provides a pharmaceutical composition for preventing or treating neurological diseases comprising: (a) an extract of a mixture of *Euphoria longan* fruit, red sage and *Gastrodia elata* as an active ingredient; and (b) a pharmaceutically acceptable carrier.

In another general aspect, the present disclosure provides a food composition for improving neurological diseases comprising an extract of *Euphoria longan* fruit, red sage and *Gastrodia elata* as an active ingredient.

In still another general aspect, the present disclosure provides a method for preventing or treating neurological diseases.

The inventors of the present disclosure have explored natural materials capable of preventing or treating neurological diseases, especially dementia or memory impairment, that can be quickly absorbed into the body without adverse effects. As a result, they have found out that a composition including an extract of *Euphoria longan* fruit, red sage and *Gastrodia elata* improves memory impairment and effectively protects nerve cells from substances causing neurological diseases, particularly dementia.

The present composition comprises an extract of a mixture of *Euphoria longan* fruit, red sage and *Gastrodia elata* as an active ingredient. It would be appreciated by one of skill in the art that the phrase used herein "an extract of a mixture of *Euphoria longan* fruit, red sage and *Gastrodia elata*" encompasses not only an extract obtained from a mixture of *Euphoria longan* fruit, red sage and *Gastrodia elata* but also a mixture of extracts obtained from *Euphoria longan* fruit, red sage and *Gastrodia elata*, respectively. Preferably, the phrase "an extract of a mixture of *Euphoria longan* fruit, red sage and *Gastrodia elata*" refers to an extract obtained from a mixture of *Euphoria longan* fruit, red sage and *Gastrodia elata*.

The characteristics and specific effects of the *Euphoria longan* fruit, red sage and *Gastrodia elata* used in the present disclosure are as follows.

*Euphoria longan* fruit is obtained by drying the aril of *Euphoria longan* Steud., an evergreen tree in the family Sapindaceae. It has long been known to be effective in strengthening the heart and pancreas, replenishing qi and blood, and tranquilizing the mind. According to the book on medicinal plants, Shennong Bencaojing, *Euphoria longan* fruit controls the sinister qi of the five viscera, tranquilizes the mind, sharpens appetite and promotes digestion (Chang-Min Kim et al., Grand Dictionary of Chinese Medicine, 3194-3196, 2004).

Red sage (*Salvia miltiorrhiza* BGE) is a perennial plant in the family Lamiaceae. The dried root and rhizome of red sage are known to be effective in treating chest and hypochondriac pain, numb pain caused by wind and dampness, abdominal pain and swelling, and menstrual pain by promoting blood flow and removing stasis (Hocheol Kim, Herbal Pharmacology, 332-333, 2004).

*Gastrodia elata* is a saprophytic perennial herb in the family Orchidaceae. The dried tuber of *Gastrodia elata* BL has been used to treat various convulsive diseases and nervous system disorders such as headache, dizziness, numbness, etc. by regulating the liver qi (Chang-Min Kim et al., Grand Dictionary of Chinese Medicine, 4105-4110, 2004; Byung-Soo Kang et al., Herbology, 504-505, 2000).

As used herein, the term "*Euphoria longan* fruit extract" refers to an extract obtained from the aril of *Euphoria longan* Steud. The term "red sage extract" refers to an extract obtained from various parts (e.g., root, rhizome, fruit, stem, leaf and flower) of red sage. Specifically, the red sage extract may be an extract obtained from the root or rhizome of red sage. The term "*Gastrodia elata* extract" refers to an extract obtained from various parts (e.g., root, tuber, fruit, stem, leaf and flower) of *Gastrodia elata*. Specifically, the *Gastrodia elata* extract refers to an extract obtained from the tuber of *Gastrodia elata*.

The extract used in the present disclosure may be obtained using extraction solvents known in the art, specifically, (a) water, (b) $C_1$-$C_4$ anhydrous or aqueous low alcohol (e.g., methanol, ethanol, propanol, butanol, n-propanol, isopropanol, n-butanol, etc.), (c) a mixture of the low alcohol with water, (d) acetone, (e) ethyl acetate, (f) chloroform, (g) 1,3-butylene glycol, (h) hexane, (i) diethyl ether or (j) butyl acetate.

The extracts of *Euphoria longan* fruit, red sage and *Gastrodia elata* of the present disclosure also include ones obtained after purification of the extracts obtained using the above-described solvents. For example, the extracts obtained after various purification processes such as filtration through ultrafiltration membrane having a predetermined molecular weight cut-off value, separation by various chromatographic techniques (based on size, charge, hydrophobicity or affinity), etc. are included in the extracts of *Euphoria longan* fruit, red sage and *Gastrodia elata* of the present disclosure.

The extracts of *Euphoria longan* fruit, red sage and *Gastrodia elata* of the present disclosure may be prepared into powder form through further processes such as distillation under reduced pressure followed by freeze drying or spray drying.

In an exemplary embodiment of the present disclosure, the mixture used in the composition of the present disclosure further comprises a plant for improving blood circulation. The plant for improving blood circulation includes any one known to be effective in invigorating or improving blood circulation for enabling fast and effective absorption of the composition of the present disclosure into the body.

More specifically, the mixture used in the composition of the present disclosure may further comprise a plant for improving blood circulation which is selected from a group consisting of *ophiopogon* root, turmeric, *Cnidium officinale, Angelica gigas*, peach kernel, safflower, *Achyranthes japonica, Caesalpinia sappan*, frankincense, motherwort, *Curcuma longa*, bur-reed rhizome, honey locust thorn and myrrh (Byung-Soo Kang et al., Herbology, 408-441, 2000). More specifically, the plant for improving blood circulation used in the present disclosure may be *ophiopogon* root or turmeric.

Among the plants for improving blood circulation, *ophiopogon* root and turmeric will be described in detail.

*Ophiopogon* root is the dried tuberous root of *Liriope platyphylla* Wang et Tang or *Ophiopogon japonicas* Ker Gawl, which are perennial in the family Liliaceae. *Ophiopogon* root is moist in nature and is known to treat dry cough, hematemesis, heartburn, hydrodipsomania, or the like by generating body fluid, moistening dryness and cooling down the excessive heart qi (Chang-Min Kim et al., Grand Dictionary of Chinese Medicine, 1262-1269, 2004; Byung-Soo Kang et al., Herbology, 588-589, 2000). Also, it is known to treat dry cough caused by dryness of the lungs, hematemesis, hemoptysis, fever caused by lack of energy and fatigue, thirst, throat and mouth dryness caused by fever, and constipation (Chang-Min Kim et al., Grand Dictionary of Chinese Medicine, 1264, 2004). In addition, the *oph-*

*iopogon* root is known to have antioxidant effect, promote blood circulation in the coronary arteries, improve contraction of the heart muscles and enhance immunity (Korean Patent No. 10-0894415) and is also known to have a detoxifying effect of treating eye yellowing and body blackening caused by fever (Korean Patent Publication No. 10-2004-15828).

More specifically, the *ophiopogon* root further included in the composition of the present disclosure may be the root of *Ophiopogon japonicas*.

Turmeric is the tuberous root of *Curcuma longa* Linne, *Curcuma aromatica* Salisbury or *Curcuma zedoaria* (Berg.) Rosc, of the family Zingiberaceae, and contains curcumin, turmerone, zingiberene, etc. Traditionally, turmeric has been known to promote the secretion of gastric juice, promote urination, have a detoxifying effect, promote regeneration of liver cells and have anti-inflammatory and antioxidant effects (Chang-Min Kim et al., Grand Dictionary of Chinese Medicine, 3282-3286, 1997). Also, turmeric is known to help blood circulation and remove stasis (Byung-Soo Kang et al., Herbology, 408-441, 2000).

In an exemplary embodiment of the present disclosure, the plant for improving blood circulation helps blood circulation and exhibits detoxifying effect when administered into the body.

The plant for improving blood circulation used in the present disclosure helps blood circulation by promoting blood flow, improving contraction of heart muscles or removing stasis and has a detoxifying effect of controlling or removing toxic substances absorbed or accumulated in the body.

The content of the *ophiopogon* root or turmeric of the extract in the composition of the present disclosure is not particularly limited as long as the desired effect of blood circulation improvement or detoxification is achieved. Those skilled in the art will be able to determine the content of the further included plant to suit the purpose of the present disclosure.

Specifically, the *ophiopogon* root or turmeric of the extract may be included in an amount of 1-99 wt %, more specifically 10-80 wt %, most specifically 30-70 wt %, based on the total weight of the mixture, but is not limited thereto.

The pharmaceutical composition of the present disclosure comprises a pharmaceutically effective amount of an extract of *Euphoria longan* fruit, red sage and *Gastrodia elata*. As used herein, the term "pharmaceutically effective amount" refers to an amount sufficient to achieve the effect or activity of the extract of *Euphoria longan* fruit, red sage and *Gastrodia elata* and is not particularly limited as long as the purpose of the present disclosure can be achieved.

Specifically, in the composition of the present disclosure, the *Euphoria longan* fruit may be included in an amount of 1-99 wt %, more specifically 10-80 wt %, most specifically 20-60 wt %, based on the total weight of the mixture, the *Gastrodia elata* may be included in an amount of 0.1-99 wt %, more specifically 1-80 wt %, most specifically 5-60 wt %, based on the total weight of the mixture, and the red sage may be included in an amount of 0.1-99 wt %, more specifically 0.5-80 wt %, most specifically 1-50 wt %, based on the total weight of the mixture, although not being limited thereto.

When the composition of the present disclosure is prepared as a pharmaceutical composition, the pharmaceutical composition of the present disclosure comprises a pharmaceutically acceptable carrier. The pharmaceutically acceptable carrier included in the pharmaceutical composition of the present disclosure may be one commonly used in the art. Examples include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., but are not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable carriers and formulations are described in detail in Remington's Pharmaceutical Sciences (19th ed., 1995).

The pharmaceutical composition of the present disclosure may be administered orally or parenterally, specifically orally.

An appropriate dosage of the pharmaceutical composition of the present disclosure may be determined variously depending on such factors as preparation method, administration method, age, body weight and sex of the patient, pathological condition, diet, administration time, administration route, excretion rate or response sensitivity. A general dosage of the pharmaceutical composition of the present disclosure for an adult is 0.001-1000 mg/kg.

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

The composition of the present disclosure may also be provided as a food composition.

When the composition of the present disclosure is prepared as a food composition, the composition of the present disclosure may comprise, in addition to the extract of the mixture of *Euphoria longan* fruit, red sage and *Gastrodia elata* as an active ingredient, ingredients commonly added for preparation of food. For example, proteins, carbohydrates, fats, nutrients, seasoning or flavors may be added. The carbohydrate may be, for example, a sugar such as a monosaccharide, e.g. glucose, fructose, etc., a disaccharide, e.g. maltose, sucrose, oligosaccharide, etc. or a polysaccharide, e.g. dextrin, cyclodextrin, etc. or a sugar alcohol such as xylitol, sorbitol, erythritol, etc. The flavor may be a natural flavor [thaumatin, stevia extract (e.g. rebaudioside A, glycyrrhizin, etc.)] or a synthetic flavor (saccharin, aspartame, etc.).

For example, when the food composition of the present disclosure is prepared as a drink, it may further comprise, in addition to the extract of the mixture of *Euphoria longan* fruit, red sage and *Gastrodia elata*, citric acid, high-fructose corn syrup, sugar, glucose, acetic acid, malic acid, fruit juice, eucommia extract, jujube extract, licorice extract, or the like.

The composition of the present disclosure may be used to prevent or treat various neurological diseases. Specifically, the composition of the present disclosure may be used to prevent or treat degenerative nerve disease or mental disorder.

More specifically, the degenerative nerve disease may be dementia, Alzheimer's disease, Huntington's disease, Parkinson's disease or amyotrophic lateral sclerosis.

As used herein, the term "dementia" refers to a disease, disorder or condition characterized by severe loss of cognitive ability. Dementia can be classified into Alzheimer's dementia, vascular dementia and other dementia.

The composition of the present disclosure is effective in treating Alzheimer's disease. Excess amyloid β peptide buildup is associated with Alzheimer's disease. Decreasing amyloid β in the neuritic space slows the progress of Alzheimer's disease. Although the formation process of amyloid β has not been completely elucidated scientifically, the composition of the present disclosure can prevent or treat Alzheimer's disease by inhibiting the detrimental nervous insult of amyloid β as demonstrated in the following examples.

Vascular dementia is the second most common form of dementia. This disease is caused by the narrowing or blockage of blood vessels supplying blood to the brain. Also, repeated strokes may lead to vascular dementia. The composition of the present disclosure may be useful in the treatment of vascular dementia.

More specifically, the mental disorder may be depression, schizophrenia or posttraumatic stress disorder. Depression is a mental disorder that can be caused by stress. It often leads to an extreme result such as suicide and is recognized as a very important disease owing to high relapse and fast increase. Disorders of brain neurotransmitters such as adrenaline, dopamine or serotonin are known as the cause of depression. Depression is also accompanied by brain damage such as hippocampal atrophy, suppressed neurogenesis in adults, or the like. Although tricyclic antidepressants (TCAs) are currently known representative antidepressants, they have many adverse effects. In particular, amitriptyline, which is widely prescribed inside and outside Korea, has various adverse effects. In the 1980s, the selective serotonin reuptake inhibitor (SSRI) fluoxetine was developed in the USA. With reduced adverse effects, greatly improved compliance and reduced treatment failure, it ranked 7th among the world's 20 best-selling drugs in 1996. However, the SSRIs do not show big difference from TCAs in terms of effect and have severe drug interaction problems. The extract of *Euphoria longan* fruit, red sage and *Gastrodia elata* of the present disclosure prevent the degeneration of pyramidal cells in the dentate gyrus of the hippocampus from nervous insult, for example, caused by amyloid β, as demonstrated in the following examples. This suggests the potential of the composition of the present disclosure as antidepressant.

In another general aspect, the present disclosure provides a food composition for improving brain or cognitive function comprising an extract of *Euphoria longan* fruit, red sage and *Gastrodia elata* extracts as an active ingredient.

In still another general aspect, the present disclosure provides a method for improving brain or cognitive function, comprising: administering to a subject a composition comprising an extract of *Euphoria longan* fruit, red sage and *Gastrodia elata* as an active ingredient.

In an exemplary embodiment of the present disclosure, the mixture used in the composition of the present disclosure further comprises a plant for improving brain or cognitive function selected from learning ability, memory and concentration. More specifically, the mixture used in the composition of the present disclosure may further comprise a plant for improving memory impairment.

Memory impairment precedes Alzheimer's disease. Acetylcholine deficiency due to the degeneration of cholinergic nerve cells is one major cause and increased activity of acetylcholinesterase (AChE) aggravates the symptom. Although AChE inhibitors (tacrine, donepezil, rivastigmine and galantamine) have been developed as treatment for Alzheimer's disease, it is difficult to directly regenerate the brain cells or inhibit damage to the brain cells. Since the composition of the present disclosure comprising the extract of *Euphoria longan* fruit, red sage and *Gastrodia elata* as an active ingredient reduces the activity of AChE and suppresses nerve damage caused by nervous insult with few adverse effects to the human body, it may be very usefully used for improvement of memory impairment.

ADVANTAGEOUS EFFECTS

The features and advantages of the present disclosure may be summarized as follows:

(a) The present disclosure provides a composition for preventing or treating neurological diseases comprising an extract of *Euphoria longan* fruit, red sage and *Gastrodia elata*. Since it protects nerve cells from nervous insult caused by, for example, amyloid β, it is very effective in preventing or treating neurological diseases, especially dementia.

(b) The composition of the present disclosure has a very superior effect of improving memory.

(c) The composition of the present disclosure can be quickly absorbed into the human body with few adverse effects.

The examples and experiments will now be described. The following examples and experiments are for illustrative purposes only and not intended to limit the scope of the present disclosure.

EXAMPLES

Experimental Design

Various experiments were performed to investigate the effect of an extract of *Euphoria longan* fruit, red sage and *Gastrodia elata* on treatment of dementia and improvement of memory impairment. In order to evaluate the effect of HX107M (see Test Example 1) on the cholinergic neurotransmission related with memory impairment found in patients with dementia, inhibition of the activity of acetylcholinesterase (AChE) was measured. Also, using a rat model in which damage of nerve cells was induced by administering amyloid β peptide, known to induce dementia, into the cerebral ventricle, the effect of HX107N on learning ability and memory was evaluated through water maze test and passive avoidance test, and the damage of nerve cells was identified by histological examination.

Preparation Example 1

Preparation of Extract Mixture of *Euphoria longan* Fruit, Red Sage and *Gastrodia Elata*

All herbs used were purchased from a market specializing in herbs (HUMANHERB, Korea). Dried *Euphoria longan* fruit, red sage and *Gastrodia elata* were mixed with the weight proportion described in Table 1. After adding 10 weight equivalents of water, reflux extraction was performed at about 90-100° C. for 3 hours. The extract was filtered, concentrated at 60° C. and freeze-dried to obtain extract in powder form.

TABLE 1

| Extract mixture | Euphoria longan fruit | Gastrodia elata | Red sage |
|---|---|---|---|
| No. 1 | 3 | 1 | 3 |
| No. 2 | 2.9 | 4 | 0.1 |
| No. 3 | 5.4 | 0.1 | 1.5 |

Table 1 shows the weight proportions of the three herbs.

Preparation Example 2

Preparation of Individual Extracts

After adding 10 weight equivalents of water to dried *Euphoria longan* fruit, red sage or *Gastrodia elata* (10 g each), reflux extraction was performed at about 90-100° C. for 3 hours. The extracts were filtered, concentrated at 60° C. and freeze-dried to obtain four extracts in powder form.

Preparation Example 3

Preparation of Extract Mixture Further Comprising Herb for Improving Blood Circulation Dried *Ophiopogon japonicas* or turmeric was mixed with *Euphoria longan* fruit, red sage and *Gastrodia elata* at a weight ratio of 5:3:3:1. After adding 10 weight equivalents of water, reflux extraction was performed at about 90-100° C. for 3 hours. The extract was filtered, concentrated at 60° C. and freeze-dried to obtain extract in powder form.

TABLE 2

| Extract mixture | Euphoria longan fruit | Red sage | Gastrodia elata | Ophiopogon japonicas | Turmeric |
|---|---|---|---|---|---|
| No. 4 | 3 | 3 | 1 | 0 | 5 |
| No. 5 | 3 | 3 | 1 | 5 | 0 |

Table 2 shows the weight proportions of the five herbs.

Test Example 1

AChE Activity Inhibition Effect According to Mixing Proportion of Extracts

AChE activity assay was performed according to Ellman's method (Ellman et al., Biochem Pharmacol 7: 88-95 (1961)) using the extracts from the mixtures prepared in Preparation Example 1. In order to obtain AChE, the brain of a 5-week-old male ICR mouse (Orient Bio, Korea) was extracted after acclimatization for a week. The brain was homogenized to 10 volume equivalents of the brain using 12.5 mM sodium phosphate buffer (pH 7.0). The homogenate was centrifuged at 3000 rpm for 10 minutes at 4° C. and the supernatant was obtained. For in vitro AChE activity assay, buffer, 75 mM acetylthiocholine iodide and 10 mM 5,5'-dithiobis(2-nitrobenzoic acid) (DNTB) were added to a 96-well microplate and the plate was treated with each extract at 5 mg/mL and 10 mg/mL. Then, after adding the supernatant obtained from the mouse to the plate, reaction was incubated at room temperature for 10 minutes in the dark. After the reaction was completed, the change in absorbance at 405 nm was measured for 40 minutes with 2-minute intervals. Extract No. 1 had the best effect and was named HX107M.

TABLE 3

|  | 5 mg/mL | 10 mg/mL |
|---|---|---|
| No. 1 | 32.88 | 50.50 |
| No. 2 | 11.40 | 22.28 |
| No. 3 | 22.22 | 39.56 |

Table 3 shows AChE activity inhibition effect (%) according to mixing proportions of the extracts.

Test Example 2

Figure 1:
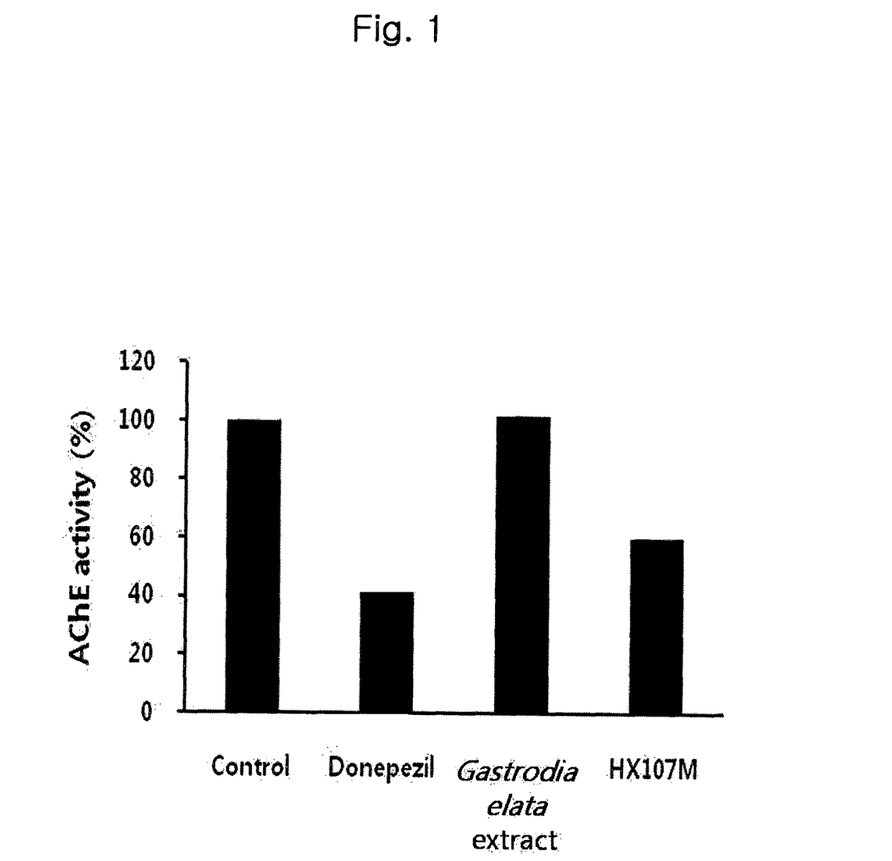
FIG. 1 shows the effect of treatment of the brain of a male mouse with donepezil, *Gastrodia elata* extract or HX107M on the activity of acetylcholinesterase (AChE).

Comparison of AChE Activity Inhibition Effect of HX107M and *Gastrodia Elata* Extract AChE activity assay was performed according to Ellman's method (Ellman et al., Biochem Pharmacol 7: 88-95, (1961)) using HX107M and *Gastrodia elata* extract. In order to obtain AChE, the brain of a 5-week-old male ICR mouse (Orient Bio, Korea) was extracted after acclimatization for a week. The brain was homogenized to 10 volume equivalents of the brain using 12.5 mM sodium phosphate buffer (pH 7.0). The homogenate was centrifuged at 3000 rpm for 10 minutes at 4° C. and the supernatant was obtained. For in vitro AChE activity assay, buffer, 75 mM acetylthiocholine iodide and 10 mM 5,5'-dithiobis(2-nitrobenzoic acid) (DNTB) were added to a 96-well microplate and the plate was treated with HX107M and *Gastrodia elata* extract at 5.83 mg/mL and 0.83 mg/mL. Then, after adding the supernatant obtained from the mouse to the plate, reaction was incubated at room temperature for 10 minutes in the dark. After the reaction was completed, the change in absorbance at 405 nm was measured for 40 minutes with 2-minute intervals. As a result, HX107M showed an AChE activity inhibition effect of 40.35%, whereas the *Gastrodia elata* extract showed no AChE activity inhibition effect (FIG. 1).

Test Example 3

Comparison of AChE Activity Inhibition Effect of HX107M and HX107N

*Ophiopogon japonicas* or turmeric, which is well known to improve blood circulation, was mixed with HX107M and the effect on inhibition of AChE activity of HX107M was investigated. Of the two candidates, *Ophiopogon japonicas* was finally selected since it further has the detoxifying effect and is capable of improving the safety of composition of the present disclosure. The mixture extract No. 5 prepared in Preparation Example 3 was named as HX107N.

Figure 2:
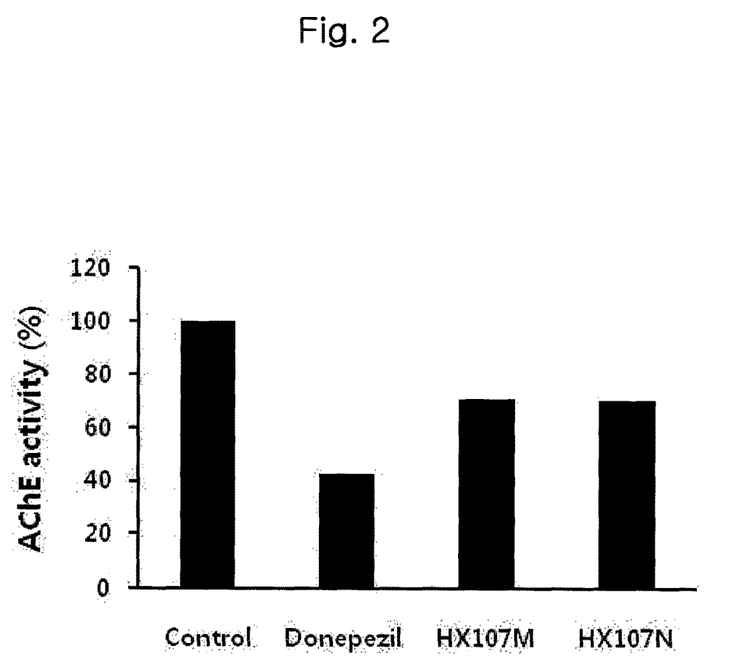
FIG. 2 shows the effect of treatment of the brain of a male mouse with donepezil, HX107M, HX107N including *ophiopogon* root on the activity of AChE.

Experiment was carried out as in Test Example 2 by treating with HX107M and HX107N at 2.92 mg/mL and 5 mg/mL, respectively. As a result, HX107M and HX107N showed comparable AChE inhibition activity of 29.02% and 29.83% (FIG. 2). This suggests that the addition of *ophiopogon* root does not significantly affect the AChE inhibition activity.

For increased applicability in humans considering adverse effects, the following experiments using animal model were carried out using HX107N which further comprises *Ophiopogon japonicas* having blood circulation improving and detoxifying effects.

Test Example 4

Comparison of AChE Activity Inhibition Effect of HX107N and Red Sage Extract

Figure 3:
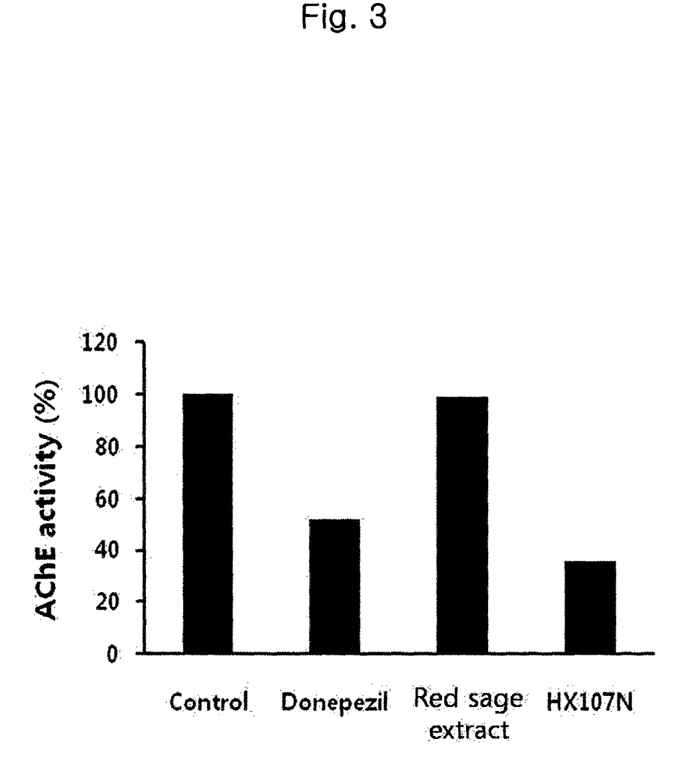
FIG. 3 shows the effect of oral administration of donepezil, HX107N or red sage extract on the activity of AChE in the brain of a male mouse.

The AChE inhibition activity of HX107N and red sage extract was compared as follows. 5-week-old male ICR mice (Orient Bio, Korea) were purchased and acclimatized for a week. For in vivo AChE activity assay, control substance (donepezil 1 mg/kg), HX107N (200 mg/kg) or red sage extract (50 mg/kg) was orally administered once to the mice (3 per each group). 6 hours later, the hippocampus was isolated and homogenized using 1 M phosphate buffer (pH 8.0). The in vivo AChE activity of the obtained homogenate was measured using the Amplex red assay kit (Molecular Probe, USA). As a result, HX107N showed an AChE activity inhibition effect of about 64.4%, whereas the red sage extract showed no AChE activity inhibition effect (FIG. 3).

of the animal. The group to which 200 mg/kg HX107N had been administered for 4 weeks showed significantly reduced damage to the spatial memory and learning ability.

TABLE 4

| Trails | Non-treated | Aβ + saline | Aβ + red ginseng | Aβ + HX107N 10 mg/kg | Aβ + HX107N 100 mg/kg | Aβ + HX107N 200 mg/kg |
|---|---|---|---|---|---|---|
| 1 | 85.79 ± 4.21 | 86.48 ± 3.08 | 87.69 ± 1.54 | 90.00 ± 0.00 | 84.64 ± 4.12 | 89.90 ± 0.10 |
| 2 | 74.88 ± 8.83 | 73.08 ± 7.02 | 86.83 ± 2.45 | 76.27 ± 9.18 | 78.29 ± 6.38 | 82.08 ± 5.39 |
| 3 | 74.38 ± 8.53 | 84.66 ± 3.73 | 75.40 ± 8.07 | 86.44 ± 2.14 | 75.27 ± 6.18 | 73.42 ± 9.01 |
| 4 | 67.69 ± 9.3 | 76.60 ± 7.44 | 68.31 ± 6.53 | 74.69 ± 8.36 | 64.52 ± 8.28 | 52.43 ± 9.71 |
| 5 | 67.00 ± 8.79 | 71.67 ± 9.12 | 62.86 ± 6.59 | 71.59 ± 8.37 | 56.72 ± 9.84 | 50.94 ± 8.58 |
| 6 | 69.36 ± 7.79 | 69.80 ± 10.29 | 45.77 ± 8.37 | 64.76 ± 8.98 | 50.39 ± 9.78 | 38.66 ± 9.75# |
| 7 | 44.04 ± 6.82 | 50.30 ± 9.73 | 40.79 ± 7.48 | 57.63 ± 10.17 | 45.58 ± 10.04 | 44.59 ± 9.10 |
| 8 | 22.19 ± 3.08 | 42.77 ± 9.69 | 32.03 ± 6.46 | 35.59 ± 9.40 | 30.12 ± 7.35 | 27.94 ± 7.88 |
| 9 | 21.22 ± 3.36 | 30.25 ± 8.05 | 21.95 ± 6.42 | 25.05 ± 5.47 | 21.75 ± 4.14 | 15.97 ± 2.67 |
| 10 | 12.02 ± 1.90 | 19.61 ± 2.63* | 16.02 ± 3.58 | 17.52 ± 3.13 | 15.32 ± 2.86 | 9.64 ± 0.85## |

Table 4 shows the spatial memory improving effect of HX107N in the water maze test.
The symbols denote the following significance.
p < 0.05,
p < 0.01.
*p < 0.05 vs. non-treated group.

Test Example 5

Water Maze Test for Testing Spatial Memory Improving Effect of HX107N in Rat Model with Dementia Induced by Amyloid β

Figure 4:
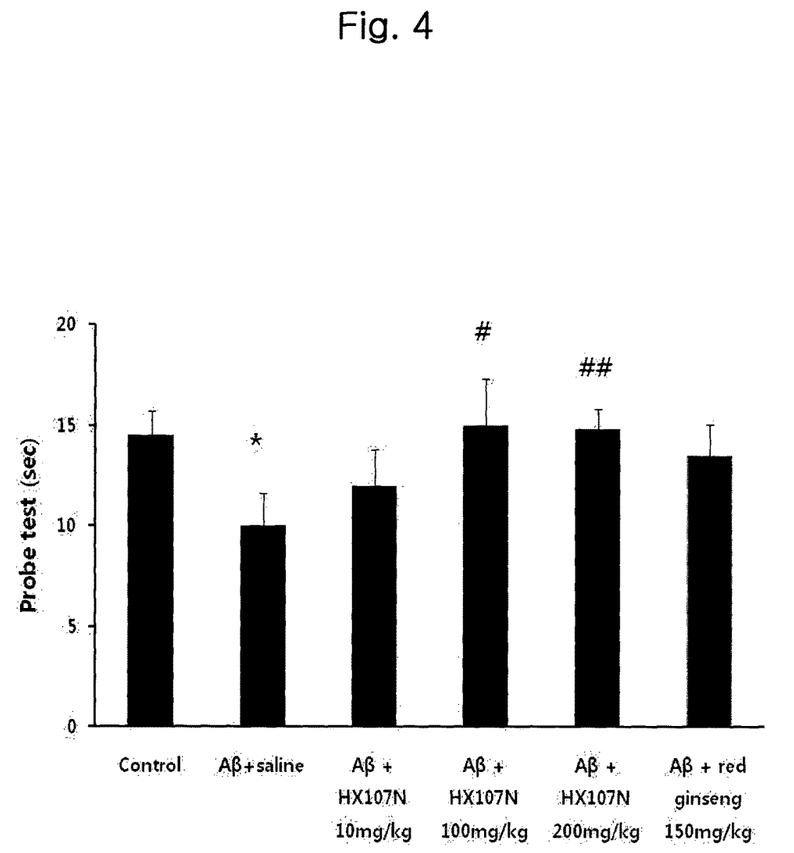
FIG. 4 shows the effect of HX107N on improvement in learning ability and memory in the probe test after administration of amyloid β into the cerebral ventricle. Symbols # and ## respectively denote significance at $p<0.05$ and $p<0.01$ and * denotes comparison with the non-treated group at $p<0.05$.

60 male Sprague-Dawley rats (Samtako Bio Korea, Korea) were purchased and acclimatized for 7 days. All test animals were allowed free access to food and water in a cage maintained at constant temperature and humidity, under a 12-hour light/dark cycle. The 60 rats were grouped into 6 groups (10 per each group) and were orally administered with HX107N (10, 100 and 200 mg/kg), red ginseng (150 mg/kg, Korea Ginseng Corp., Korea) or saline, as control, for 4 weeks. Then, 2.2 nM amyloid $\beta_{1\text{-}42}$ peptide (Sigma, USA) was injected into the cerebral ventricle of the rats using a stereotaxic apparatus to induce dementia. One week later, water maze test was carried out to test spatial memory and learning ability. First, an escape platform was prepared at the center of a quadrant of a water maze and an opaque liquid was filled to hide the platform. For 5 days, twice a day, escape latency which is the time spent until the rat reaches the escape platform was recorded from different starting points. The time limit was 90 seconds. When the rat could not find the escape platform until that time, it was placed on the escape platform for 15 seconds to learn where the platform is located. After the final test, the escape platform was removed. Then, the animal was placed in the water maze and the time during which it remained in the quadrant where the escape platform had been was measured for 30 seconds (probe test). As a result, it was confirmed that the administration of amyloid β into the cerebral ventricle had a negative effect in the spatial memory and learning ability Also in the probe test carried out after removing the escape platform, it was confirmed that the administration of amyloid β into the cerebral ventricle had a significantly negative effect in the spatial memory and learning ability of the animal. The groups to which 100 and 200 mg/kg HX107N had been administered for 4 weeks showed significant improvement (FIG. 4).

Test Example 6

Passive Avoidance Test for Testing Memory Improving Effect of HX107N in Rat Model with Dementia Induced by Amyloid β

Figure 5:
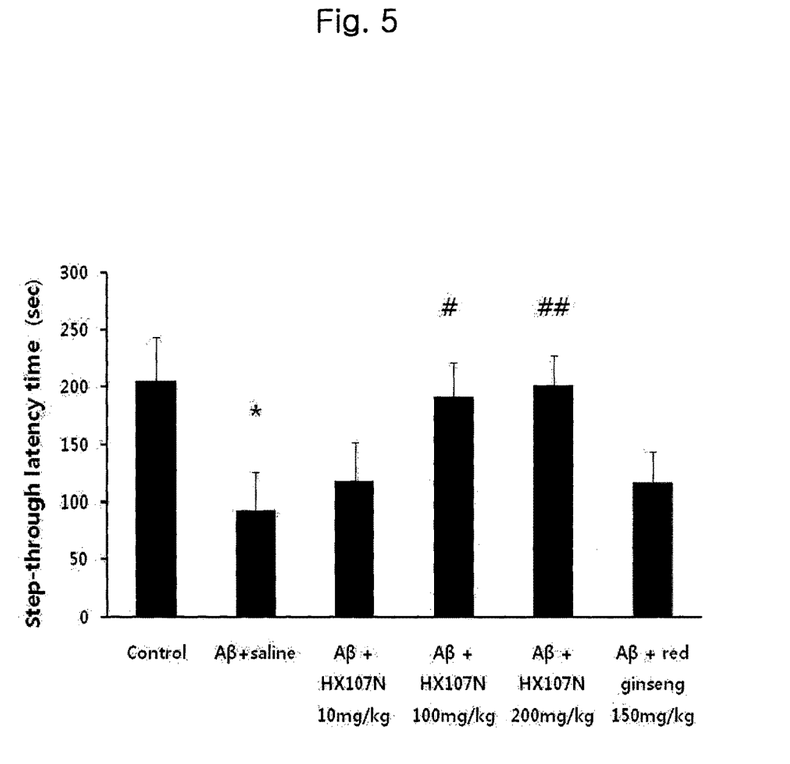
FIG. 5 shows the effect of HX107N on improvement in learning ability and memory in the passive avoidance test after administration of amyloid β into the cerebral ventricle. Symbols # and ## respectively denote significance at $p<0.05$ and $p<0.01$ and * denotes comparison with the non-treated group at $p<0.05$.

60 male Sprague-Dawley rats (Samtako Bio Korea, Korea) were purchased and acclimatized for 7 days. All test animals were allowed free access to food and water in a cage maintained at constant temperature and humidity, under a 12-hour light/dark cycle. The 60 rats were grouped into 6 groups (10 per each group) and were orally administered with HX107N (10, 100 and 200 mg/kg), red ginseng (150 mg/kg, Korea Ginseng Corp., Korea) or saline, as control, for 4 weeks. Then, 2.2 nM amyloid 1-42 peptide was injected into the cerebral ventricle of the rats using a stereotaxic apparatus to induce dementia. One week later, passive avoidance test was carried out to test memory. As a result, it was found out that amyloid β resulted in the decline of memory, with 205.12±34.69 seconds of latency time for the non-treated group and 93.48±32.82 seconds of latency time for the amyloid β-administered group, within the time limit of 300 seconds. In contrast, the group treated with HX107N showed significant improvement in memory, with 190.90±30.26 seconds of latency time for 100 mg/kg and 201.05±25.84 seconds of latency time for 200 mg/kg (FIG. 5).

Test Example 7

Histological Examination of Hippocampus in Rat Model with Dementia Induced by Amyloid β

Figure 6:
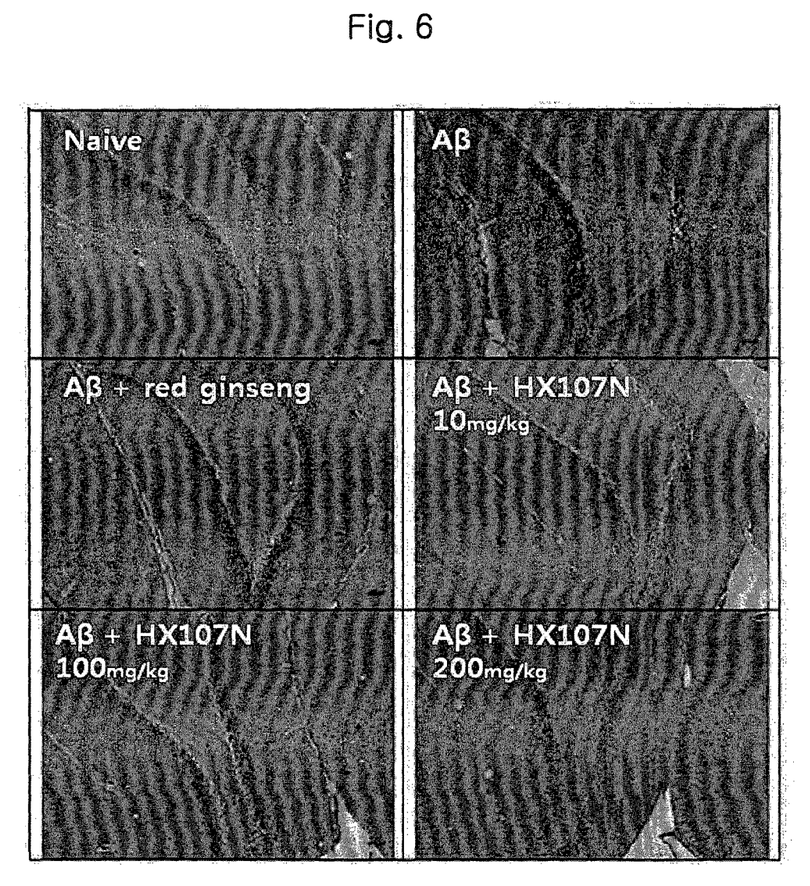
FIG. 6 shows the effect of HX107N on inhibition of brain damage in histological examination after administration of amyloid β into the cerebral ventricle.

After the behavioral tests were completed, the rats were anesthetized with diethyl ether and perfused with saline through the heart. Then, the brain was taken out and fixed in 10% neutral-buffered formalin. The degree of degeneration of the nerve cells in the hippocampus was observed by hematoxylin & eosin staining. As a result, the group treated with amyloid β showed degeneration of pyramidal cells, which are involved in memory, in the dentate gyrus of the hippocampus, as compared to the non-treated group. The group treated with 200 mg/kg HX107N showed less damage (FIG. 6).

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

What is claimed is:

1. A method for treating neurological diseases, comprising: administering to a subject suffering from a neurological disease a composition comprising an extract of a mixture consisting of 3 parts by weight of *Euphoria longan* fruit, 3 parts by weight of red sage and 1 part by weight of *Gastrodia elata* as an active ingredient.

2. The method according to claim 1, wherein the composition is a pharmaceutical composition or food composition.

3. A method for improving brain or cognitive function, comprising: administering to a subject in need thereof a composition comprising an extract of a mixture consisting of 3 parts by weight of *Euphoria longan* fruit, 3 parts by weight of red sage and 1 part by weight of *Gastrodia elata* as an active ingredient.

4. The method of claim 1, wherein the neurological disease is selected from a group consisting of degenerative nerve disease and mental disorder.

5. The method of claim 4, wherein the degenerative nerve disease is a neurological disease selected from a group consisting of dementia, Alzheimer's disease, Huntington's disease, Parkinson's disease and amyotrophic lateral sclerosis.

6. The method of claim 4, wherein the mental disorder is selected from a group consisting of depression, schizophrenia and posttraumatic stress disorder.

7. The method of claim 3, wherein the brain or cognitive function is learning ability, memory or concentration.

8. The method of claim 7, wherein the method is for improving memory impairment.

9. The method of claim 1, wherein the mixture further comprises a plant for improving blood circulation which is selected from a group consisting of *ophiopogon* root, turmeric, *Cnidium officinale*, *Angelica gigas*, peach kernel, safflower, *Achyranthes japonica*, *Caesalpinia sappan*, frankincense, motherwort, *Curcuma longa*, bur-reed rhizome, honey locust thorn and myrrh.

10. The method of claim 9, wherein the plant for improving blood circulation is ophiopogon root or turmeric.

11. The method of claim 10, wherein the *ophiopogon* root is *Liriope platyphylla* or *Ophiopogon japonicas*.

12. The method of claim 9, wherein the plant for improving blood circulation has a detoxifying effect when administered into the body.

13. The method of claim 3, wherein the mixture further comprises a plant for improving blood circulation which is selected from a group consisting of *ophiopogon* root, turmeric, *Cnidium officinale*, *Angelica gigas*, peach kernel, safflower, *Achyranthes japonica*, *Caesalpinia sappan*, frankincense, motherwort, *Curcuma longa*, bur-reed rhizome, honey locust thorn and myrrh.

14. The method of claim 13, wherein the plant for improving blood circulation is *ophiopogon* root or turmeric.

15. The method of claim 14, wherein the *ophiopogon* root is *Liriope platyphylla* or *Ophiopogon japonicas*.

16. The method of claim 13, wherein the plant for improving blood circulation has a detoxifying effect when administered into the body.

17. The method of claim 1, wherein said composition consists of said extract of said mixture, and optionally a plant for improving blood circulation selected from the group consisting of *ophiopogon* root, turmeric, *Cnidium officinale*, *Angelica gigas*, peach kernel, safflower, *Achyranthes japonica*, *Caesalpinia sappan*, frankincense, motherwort, *Curcuma longa*, bur-reed rhizome, honey locust thorn, and myrrh, wherein the composition further consists of a pharmaceutically acceptable carrier or food.

18. The method of claim 3, wherein said composition consists of said extract of said mixture, and optionally a plant for improving blood circulation selected from the group consisting of *ophiopogon* root, turmeric, *Cnidium officinale*, *Angelica gigas*, peach kernel, safflower, *Achyranthes japonica*, *Caesalpinia sappan*, frankincense, motherwort, *Curcuma longa*, bur-reed rhizome, honey locust thorn, and myrrh, wherein the composition further consists of a pharmaceutically acceptable carrier or food.

* * * * *